United States Patent
Platz et al.

(10) Patent No.: US 9,605,365 B2
(45) Date of Patent: Mar. 28, 2017

(54) COMPRESSION ARTICLE WITH INSERT

(75) Inventors: Sascha Platz, Kleve (DE); Stefan Dittmann, Emmerich (DE); Juergen Greve, Emmerich (DE)

(73) Assignee: BSN-JOBST GMBH, Emmerich (DE)

( * ) Notice: Subject to any disclaimer, the term of this patent is extended or adjusted under 35 U.S.C. 154(b) by 121 days.

(21) Appl. No.: 13/245,008

(22) Filed: Sep. 26, 2011

(65) Prior Publication Data

US 2012/0078156 A1    Mar. 29, 2012

(30) Foreign Application Priority Data

Sep. 29, 2010  (DE) .................. 10 2010 046 945

(51) Int. Cl.
| | | |
|---|---|---|
| A61F 13/08 | (2006.01) | |
| D04B 1/26 | (2006.01) | |
| A61F 13/00 | (2006.01) | |

(52) U.S. Cl.
CPC .............. *D04B 1/265* (2013.01); *A61F 13/08* (2013.01); *A61F 2013/00238* (2013.01); *D10B 2403/0114* (2013.01); *D10B 2403/023* (2013.01); *D10B 2403/0333* (2013.01)

(58) Field of Classification Search
CPC . A61F 2013/00119; A61F 13/08; D04B 1/265
USPC ........... 602/76, 75, 60, 41; 66/172 R, 169 E, 66/169 R, 196, 198, 172 E, 171, 170
See application file for complete search history.

(56) References Cited

U.S. PATENT DOCUMENTS

| | | | | |
|---|---|---|---|---|
| 663,749 | A * | 12/1900 | Gorse | 602/60 |
| 2,052,875 | A * | 9/1936 | Gammons | 28/155 |
| RE25,046 | E * | 10/1961 | Knohl | 66/178 A |
| 3,448,595 | A * | 6/1969 | Baltzer et al. | 66/193 |
| 3,453,816 | A * | 7/1969 | Radoff | D02G 3/06 28/170 |
| 3,461,695 | A * | 8/1969 | Knohl | D04B 1/24 66/178 A |
| 3,728,875 | A | 4/1973 | Hartigan et al. | |
| 4,021,860 | A * | 5/1977 | Swallow | A41B 11/008 2/239 |
| 4,027,667 | A * | 6/1977 | Swallow | D04B 9/52 2/240 |
| 4,048,818 | A | 9/1977 | Cueman | |
| 4,172,456 | A * | 10/1979 | Zens | A61F 13/08 2/240 |
| 4,180,065 | A | 12/1979 | Bowen | |
| 4,215,684 | A * | 8/1980 | Westip | 602/76 |
| 4,632,106 | A | 12/1986 | Gamm | |

(Continued)

FOREIGN PATENT DOCUMENTS

| | | |
|---|---|---|
| DE | 36 31 022 | 3/1987 |
| DE | 86 25 798 | 1/1988 |

(Continued)

OTHER PUBLICATIONS

Medical Compression Hosiery, Quality Assurance RAL-GZ 387/1, Edition Jan. 2008, Deutsches Institut Fuer Guetesicherung Und Kennzeichnung E.V (In English).

*Primary Examiner* — Tarla Patel
(74) *Attorney, Agent, or Firm* — Michael J. Striker

(57) ABSTRACT

A compression article has an elastic base structure with an insert which is knitted double-ply and applies at least substantially a same compression pressure on a body of a wearer of an article as a base structure.

9 Claims, 2 Drawing Sheets

(56) References Cited

U.S. PATENT DOCUMENTS

| | | | |
|---|---|---|---|
| 4,679,489 A * | 7/1987 | Jasinski et al. | 91/36 |
| 4,702,091 A * | 10/1987 | Good et al. | 66/171 |
| 4,745,917 A * | 5/1988 | Hasty | D04B 1/265 |
| | | | 602/63 |
| 4,811,727 A | 3/1989 | Etienne | |
| 5,133,199 A * | 7/1992 | Parikh et al. | 66/192 |
| 5,185,000 A * | 2/1993 | Brandt et al. | 602/63 |
| 5,211,035 A | 5/1993 | Hanson, II | |
| 5,419,161 A * | 5/1995 | Bodenschatz et al. | 66/172 E |
| 7,441,419 B1 * | 10/2008 | Dollyhite | A61F 13/08 |
| | | | 66/178 A |
| 2002/0029012 A1 * | 3/2002 | Gardon-Mollard | 602/62 |
| 2006/0207296 A1 * | 9/2006 | Fujikawa | A47C 31/006 |
| | | | 66/202 |
| 2010/0168634 A1 * | 7/2010 | Leeming et al. | 602/44 |

FOREIGN PATENT DOCUMENTS

| | | |
|---|---|---|
| DE | 103 58 146 | 7/2005 |
| EP | 0 227 566 | 7/1987 |

\* cited by examiner

COMPRESSION ARTICLE WITH INSERT

CROSS-REFERENCE TO RELATED APPLICATION

The invention described and claimed hereinbelow is also described in German Patent Application DE 2010 046 945.9-45 filed on Sep. 29, 2010. This German Patent Application, whose subject matter is incorporated here by reference, provides the basis for a claim of priority of invention under 35 U.S.C. 119(a)-(d).

BACKGROUND OF THE INVENTION

The invention relates to a compression article made of an elastic base structure, wherein the base structure comprises at least one knitted insert, and the base structure and the insert are produced using at least one elastic knitting thread and/or one elastic weft thread.

Such compression articles can be gloves, stockings, stocking tights, and even joint bandages. They are used to support parts of the body, in particular extremities. The compression pressure that is produced by this article and is therapeutically necessary is usually not perceived as uncomfortable by wearers of the article. This does not apply for compression articles that extend across joints, however. When the joint is bent, folds form on the inside of the bend, which can cause constrictions, redness, or chafing of the skin. Joint bandages comprising an insert provided in the joint region have therefore already been proposed, the insert being provided with slits in the bending region to prevent folds from forming. Such a bandage is described in U.S. Pat. No. 4,632,106, for example.

Document EP 0 227 566 A1 makes known the provision of an insert made of a compressible material such as latex for reducing the formation of folds. Document DE 103 58 146 B4 describes a bandage provided with a two-ply insert in the bending region to create softer folds that do not cut into the skin to such an extreme extent, wherein no weft threads are utilized in the bending region.

In the known compression articles having reduced fold formation, however, the compression effect of the article in the region of the insert changes. This can be accepted for bandages used solely for athletic applications, but not for medical articles. For the latter, the therapeutic effect of the article must be ensured and the relevant guidelines must be met.

SUMMARY OF THE INVENTION

The problem addressed by the present invention is that of providing a compression article that can be used even for medical purposes and that prevents constrictions or chafing in the bending region of a joint when the article is worn.

The problem is solved by a compression article made of an elastic base structure, wherein the base structure comprises at least one knitted insert, and the base structure and the insert are produced using at least one elastic knitting thread and/or one elastic weft thread, characterized in that the insert is knitted double-ply and double-faced, and applies approximately the same compression pressure on the body of the article wearer as does the base structure.

Due to the double-ply design of the compression article, when the insert is positioned in the bending region of a joint, the folds formed there are fewer in number or are at least less sharp than is the case with a single-ply or classically double-faced knitted article, such as a right/right flat knitted fabric. At the same time, the compression pressure of the base structure is retained even in the region of the insert. This can be achieved, in particular, when the transverse elasticity of the insert corresponds at least approximately to that of the base structure. To this end, the base structure and the at least one insert are preferably formed of the same elastic weft thread. The elastic weft thread determines mainly the transverse elasticity of the article and therefore provides the necessary compression pressure. The weft thread is preferably disposed between the two plies of the knitted article in the region of the insert. The expressions "elastic knitting thread", "elastic weft thread" used here are based on the definitions provided in the quality assurance specification RAL-GZ 387/1. The transverse and longitudinal elasticities described are determined using the methods described in this specification.

In a preferred embodiment of the article, the two plies of the insert are interconnected at points by knitting stitches and/or tuck loops. The punctiform connection enables the weft threads to be affixed in the knitted article. At the same time, however, the two plies of the knitted article can still be displaced relative to one another to a limited extent, thereby further reducing the formation of folds in the bending region of a joint.

Further advantages are attained when the inner surface, which faces the body of the article wearer, of the at least one insert is formed using a thread material that creates a softer knitted article surface than does the thread material used to form the outer layer. The resulting soft inner surface of the insert protects the wearer's skin and is perceived as very comfortable. The outer layer, however, can be made of a non-abrasive thread material, whereby the article can be designed to be extremely insensitive to mechanical loads at least in the region of the insert.

A further measure for reducing the formation of folds is to provide the insert with greater longitudinal elasticity than the base structure. This can take place, for instance, by providing the insert with more stitch rows per longitudinal unit than the base structure.

Further advantages are attained when the two plies of the insert are formed by using an elastic thread and an inelastic thread, respectively, wherein both of these threads are plated. The elastic threads serve to produce the desired transverse elasticity and longitudinal elasticity, while the inelastic threads provide the necessary dimensional stability of the article.

In principle, the base structure and the insert can be produced using weave patterns that are the same or different. In a preferred embodiment, the base structure can be knitted using a right/right weave, and the at least one insert can be knitted using a double-ply single-jersey weave.

Furthermore, it is advantageous for the insert to be knitted into the base structure, thereby preventing the formation of seams between the insert and the base structure. Such seams often result in the formation of pressure points and chafing points which greatly impair the wearing comfort.

To create therapeutically effective compression conditions across the entire article, it is advantageous, furthermore, to route the weft threads without interruption through the base structure and the at least one insert.

The compression article can be produced on circular or flatbed knitting machines. Even when produced using a flatbed knitting machine, the articles can be produced as tubular-round knitted articles that have no seams at all and can be adapted to the anatomical details of the wearer in an optimal manner.

A preferred embodiment of a compression article according to the invention is explained in the following in greater detail with reference to the drawings.

DESCRIPTION OF THE PREFERRED EMBODIMENTS

Figure 1:
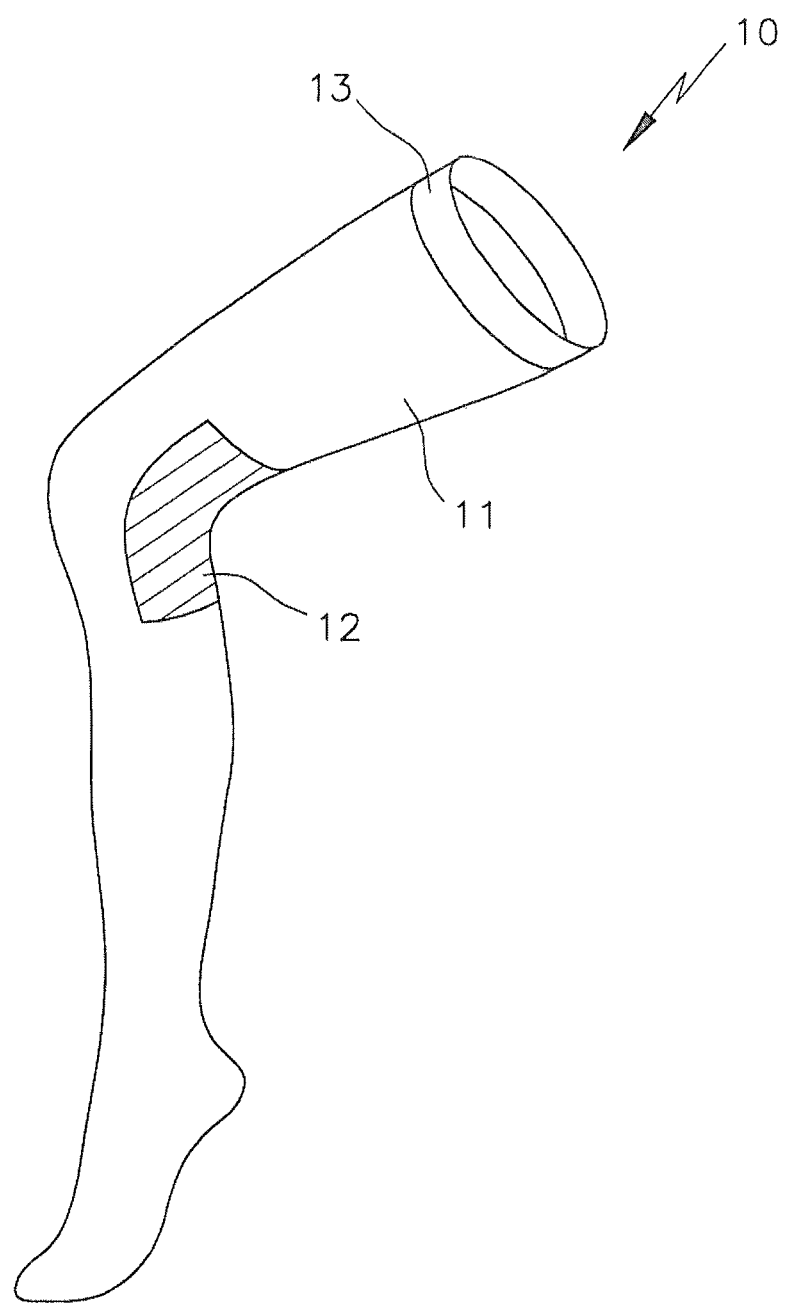
FIG. 1 shows a schematic depiction of a compression stocking having an insert.

Compression stocking 10 depicted in FIG. 1 in the form of a compression stocking comprises a tubular base structure 11 which is adapted anatomically to the shape of a leg and is provided with an insert 12 in the region of the knee bend. Insert 12 is a knitted article as well and is preferably knitted into base structure 11, i.e. it is formed at the same time. A border row 13 is provided at the upper edge and the lower edge of compression stocking 10.

Figure 2:
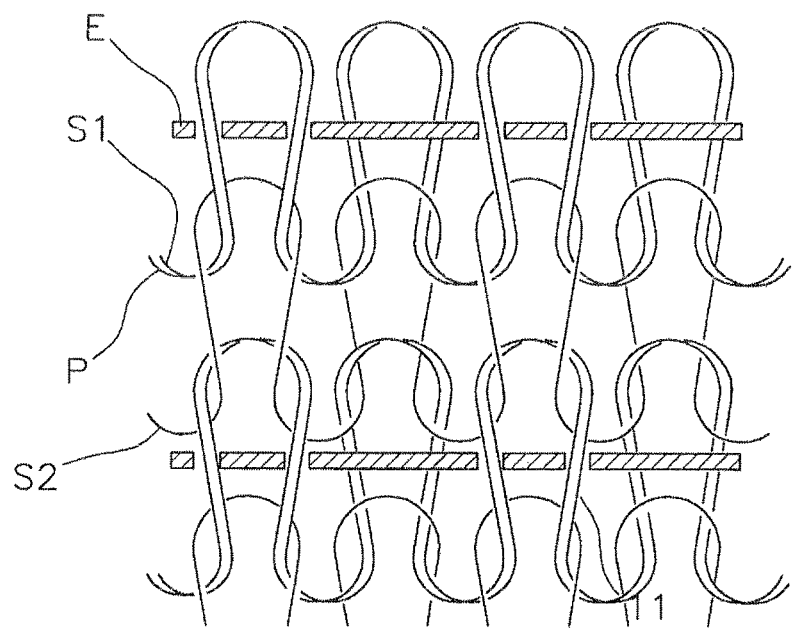
FIG. 2 shows a depiction of the weave of the base structure of the compression stocking in FIG. 1.

FIG. 2 shows one possible weave for producing base structure 11. In the example shown, this is a right/right weave into which a weft thread E has been incorporated in every other stitch row. Weft thread E is preferably elastic and provides the necessary compression pressure of compression article 10. The actual right/right weave is formed by two knitting threads S1 and S2, wherein, in the example shown, knitting thread S1 is an elastic thread, and knitting thread S2 and plating thread P are inelastic threads. Knitting thread S1 therefore provides the longitudinal elasticity of base structure 11, while knitting thread S2 and plating thread P provide the dimensional stability of base structure 11.

Figure 3:
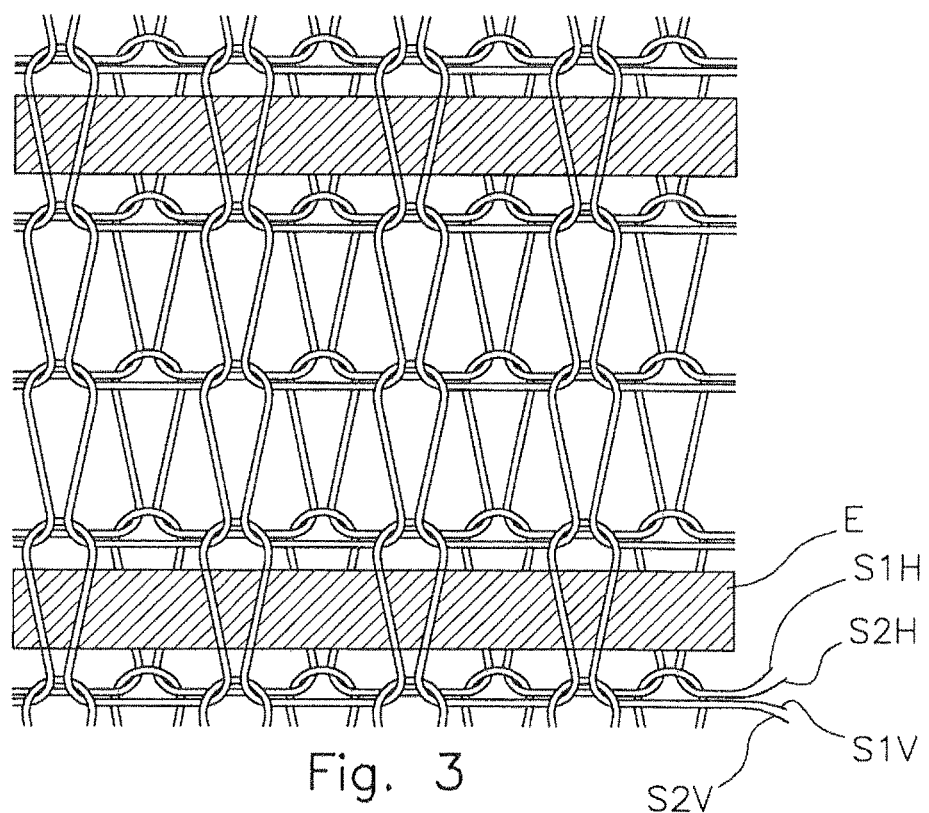
FIG. 3 shows a depiction of the weave of the insert of the compression stocking in FIG. 1.

FIG. 3 shows one possible weave for insert 12 according to the invention. This is a double-ply knitted article in a single-jersey weave, wherein weft thread E, which is also used for base structure 11, is incorporated in every third stitch row between the two plies of the knitted article. To affix weft thread E, one loop from the rear ply of the knitted article is looped around the front ply of the knitted article (not shown). Weft thread E can be retained on the underside using tuck loops. The loops, which are looped from back to front, also interconnect the two plies of the knitted article of insert 12.

The rear ply forms the inner surface which rests against the skin of the wearer of compression stocking 10. It is formed by two knitting threads S1H and S2H. Preferably, thread S1H can be an elastic thread, while thread S2H is not elastic, although it forms a particularly soft, i.e. fleeced knitted article surface. As a result, the compression stocking is very comfortable in the bending region. Folds that form there do not cause redness or chafing of the skin. The front and, therefore, outer knitted article layer is formed by knitting threads S1V and S2V. In this case as well, thread S1V can be an elastic thread, and S2V can be an inelastic thread. Threads S1H and S1V can be identical. A thread having high wear resistance can be used for threads S2V in order to increase the service life of stocking 10.

The weave shown in FIG. 3 is an enlarged view of the weave of base structure 11 shown in FIG. 2. In fact, the loops of insert 12 are smaller than those in the base structure. Weft thread E is incorporated continuously through base structure 11 and insert 12. Since the mesh size of the weave of insert 12 shown in FIG. 3 is smaller than that of the loops of the weave of base structure, which is depicted in FIG. 2, weft thread E is incorporated in every other stitch row in the base structure, and in every third stitch row in insert 12. The greater number of stitch rows per unit of length in insert 12 as compared to base structure 11 provides insert 12 with greater longitudinal elasticity than base structure 11, which further prevents the formation of folds in the bending region of compression stocking 10.

It is understood that the weaves depicted in FIGS. 2 and 3 are merely examples. Right/left weaves or left/left weaves can also be used here. The placement and selection of various knitting threads S1, S2, S1H, S2H, S1V and S2V can also differ. In addition, the shape of insert 12 can be wedge-shaped, for example, or extend around the entire circumference of compression stocking 10. Furthermore, the invention is not limited to compression stockings, and instead applies to all types of compression articles, i.e. even gloves or knee bandages or other types of joint bandages.

It will be understood that each of the elements described above, or two or more together, may also find a useful application in other types of constructions differing from the types described above.

While the invention has been illustrated and described as embodied in a compression article with insert, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compression article for use on a limb of a wearer, the compression article comprising:
   an elastic base structure; and
   at least one knitted insert arranged to cover a joint in a bending region of the limb of the wearer of the compression article,
   wherein said base structure and said at least one knitted insert are knitted with at least one elastic weft thread,
   wherein said at least one knitted insert is a knitted double-ply and double-faced insert,
   wherein said at least one knitted insert is configured to apply approximately a same compression pressure on the joint of the wearer of the compression article as does said base structure, and
   wherein said at least one elastic weft thread is routed continuously through said base structure and said at least one knitted insert.

2. The compression article as defined in claim 1, wherein said at least one knitted insert has two plies which are interconnected at points by structures selected from the group consisting knitting stitches, tuck loops, and both.

3. The compression article as defined in claim 1, wherein said at least one knitted insert has an inner ply adapted to face the body of the wearer of the article and formed with a thread material that creates a softer knitted article surface that does a thread material forming an outer layer of said at least one knitted insert.

4. The compression article as defined in claim 1, wherein said at least one knitted insert has a greater longitudinal elasticity than said base structure.

5. The compression article as defined in claim 4, wherein said at least one knitted insert has more stitch row per unit of length than said base structure.

6. The compression article as defined in claim 1, wherein said at least one knitted insert has two plies with an elastic thread and an inelastic thread, and both of said threads are plated.

7. The compression article as defined in claim 1, wherein said base structure has a right/right weave, and said at least one knitted insert has a double-ply single-jersey weave.

8. The compression article as defined in claim 1, wherein said at least one knitted insert is knitted into said base structure.

9. A compression article for use on a limb of a wearer, the compression article comprising:
- an elastic base structure configured to have a right-right weave; and
- at least one knitted insert arranged to cover a joint in a bending region of the limb of the wearer of the compression article,
- wherein said base structure and said at least one knitted insert are knitted with at least one elastic weft thread,
- wherein said at least one knitted insert is a knitted double-ply and double-faced insert,
- wherein said at least one knitted insert and is configured with a single-jersey weave and applies approximately a same compression pressure on the joint of the wearer of the compression article as does said base structure, and
- wherein said at least one elastic weft thread is routed continuously through said base structure and said at least one knitted insert.

* * * * *